United States Patent
Berka et al.

(10) Patent No.: US 8,277,385 B2
(45) Date of Patent: Oct. 2, 2012

(54) METHOD AND APPARATUS FOR NON-INVASIVE ASSESSMENT OF HEMODYNAMIC AND FUNCTIONAL STATE OF THE BRAIN

(75) Inventors: Chris Berka, Carlsbad, CA (US);
Daniel J. Levendowski, Carlsbad, CA (US); Djordje Popovic, La Jolla, CA (US); Philip R. Westbrook, Fallbrook, CA (US)

(73) Assignee: Advanced Brain Monitoring, Inc., Carlsbad, CA (US)

( * ) Notice: Subject to any disclaimer, the term of this patent is extended or adjusted under 35 U.S.C. 154(b) by 368 days.

(21) Appl. No.: 12/700,619

(22) Filed: Feb. 4, 2010

(65) Prior Publication Data
US 2010/0268096 A1 Oct. 21, 2010

Related U.S. Application Data

(60) Provisional application No. 61/149,850, filed on Feb. 4, 2009.

(51) Int. Cl.
*A61B 5/02* (2006.01)
*A61B 5/04* (2006.01)
*A61B 5/00* (2006.01)

(52) U.S. Cl. ......... 600/485; 600/504; 600/544; 600/561

(58) Field of Classification Search .................. 600/484, 600/485, 544, 561
See application file for complete search history.

(56) References Cited

U.S. PATENT DOCUMENTS

| | | | |
|---|---|---|---|
| 4,204,547 A * | 5/1980 | Allocca | .......... 600/561 |
| 4,564,022 A | 1/1986 | Rosenfeld et al. | |
| 4,841,986 A | 6/1989 | Marchbanks | |
| 4,882,287 A | 11/1989 | Holter et al. | |
| 4,971,061 A | 11/1990 | Kageyama et al. | |
| 4,984,567 A | 1/1991 | Kageyama et al. | |
| 5,047,310 A | 9/1991 | Ozaki et al. | |
| 5,117,835 A | 6/1992 | Mick | |
| 5,388,583 A | 2/1995 | Ragauskas et al. | |
| 5,617,873 A * | 4/1997 | Yost et al. | ...................... 600/561 |
| 5,919,144 A | 7/1999 | Bridger et al. | |

(Continued)

FOREIGN PATENT DOCUMENTS

WO WO9834536 8/1998

(Continued)

OTHER PUBLICATIONS

Nilsson et al., Age and gender do not influence the ability to detect respiration by photoplethysmography. J Clin Monit Comput. Dec. 2006; 20(6):pp. 431-436. Epub Oct. 11, 2006.

(Continued)

*Primary Examiner* — Patricia Mallari
*Assistant Examiner* — Tiffany Weston
(74) *Attorney, Agent, or Firm* — Procopio, Cory, Hargreaves & Savitch LLP

(57) ABSTRACT

A method and apparatus for assessment of hemodynamic and functional state of the brain is disclosed. In one embodiment, the method and apparatus includes non-invasive measurement of intracranial pressure, assessment of the brain's electrical activity, and measurement of cerebral blood flow. In some embodiments, the method and apparatus include measuring the volume change in the intracranial vessels with a near-infrared spectroscopy or other optical method, measuring the volume change in the intracranial vessels with rheoencephalography or other electrical method, and measuring the brain's electrical activity using electroencephalography.

20 Claims, 4 Drawing Sheets

U.S. PATENT DOCUMENTS

| | | |
|---|---|---|
| 5,951,477 A | 9/1999 | Ragauskas et al. |
| 5,993,398 A | 11/1999 | Alperin |
| 6,086,533 A | 7/2000 | Madsen |
| 6,117,089 A | 9/2000 | Sinha |
| 6,231,509 B1 | 5/2001 | Johnson |
| 6,245,027 B1 | 6/2001 | Alperin |
| 6,390,989 B1 | 5/2002 | Denninghoff |
| 6,413,227 B1 | 7/2002 | Yost |
| 6,457,147 B1 | 9/2002 | Williams |
| 6,589,189 B2 | 7/2003 | Meyerson |
| 6,740,048 B2 | 5/2004 | Yost |
| 6,746,410 B2 | 6/2004 | Yost |
| 6,761,695 B2 | 7/2004 | Yost |
| 6,773,407 B2 | 8/2004 | Yost |
| 7,104,958 B2 | 9/2006 | Crutchfield |
| 7,122,007 B2 | 10/2006 | Querfurth |
| 7,147,605 B2 | 12/2006 | Ragauskas |
| 2006/0206037 A1 | 9/2006 | Braxton |
| 2006/0241438 A1 | 10/2006 | Wu et al. |
| 2007/0016046 A1 | 1/2007 | Mozayeni et al. |
| 2007/0225607 A1 | 9/2007 | Wu et al. |
| 2007/0244411 A1 | 10/2007 | Jeng et al. |
| 2007/0287899 A1* | 12/2007 | Poupko et al. ............. 600/383 |
| 2008/0077023 A1 | 3/2008 | Campbell et al. |

FOREIGN PATENT DOCUMENTS

| | | |
|---|---|---|
| WO | WO0068647 | 11/2000 |
| WO | WO2007147069 | 12/2007 |

OTHER PUBLICATIONS

Nilsson et al., Respiration can be monitored by photoplethysmography with high sensitivity and specificity regardless of anaesthesia and ventilatory mode. Acta Anaesthesiol Scand. Sep. 2005; 49(8): pp. 1157-1162.

Nilsson et al., Macrocirculation is not the sole determinant of respiratory induced variations in the reflection mode photoplethysmographic signal. Physiol Meas. Nov. 2003; 24(4): pp. 925-937.

Nilsson et al., Respiratory variations in the reflection mode photoplethysmographic signal. Relationships to peripheral venous pressure. Med Biol Comput. May 2003; 41(3): pp. 249-254.

Nilsson et al., Monitoring of respiratory rate in postoperative care using a new photoplethysmographic technique. J Clin Monit Comput. 2000; 16(4): pp. 309-315.

Leonard P, Grubb NR, Addison PS, Clifton D, Watson JN. An algorithm for the detection of individual breaths from the pulse oximeter waveform. J Clin Monit Comput. Dec. 2004;18(5-6): pp. 309-312.

Magder S. How to use central venous pressure measurements. Curr Opin Crit Care. Jun. 2005;11(3): pp. 264-270.

Teng XF, Zhang YT. The effect of contacting force on photoplethysmographic signals. Physiol Meas. Oct. 2004;25(5): pp. 1323-1335.

Cox P, Johnson JO, Tobias JD. Measurement of central venous pressure from a peripheral intravenous catheter in the lower extremity. South Med J. Jul. 2005;98(7): pp. 698-702.

Nakajima K, Tamura T, Miike H. Monitoring of heart and respiratory rates by photoplethysmography using a digital filtering technique. Med Eng Phys. Jul. 1996;18, pp. 365-367.

Haba-Rubio J, Darbellay G, Herrmann FR, Frey JG, Fernandes A, Vesin JM, Thiran JP, Tschopp JM. Obstructive sleep apnea syndrome: effect of respiratory events and arousal on pulse wave amplitude measured by photoplethysmography in NREM sleep. Sleep Breath. Jun. 2005;9(2): pp. 73-81.

Cannesson M, Besnard C, Durand PG, Bohe J, Jacques D. Relation between respiratory variations in pulse oximetry plethysmographic waveform amplitude and arterial pulse pressure in ventilated patients. Crit Care. Oct. 5, 2005;9(5): pp. R562-568. Epub Aug. 23, 2005.

Johansson A, Oberg PA. Estimation of respiratory volumes from the photoplethysmographic signal. Part I: Experimental results. Med Biol Eng Comput. Jan. 1999;37(1): pp. 42-47.

Johansson A, Oberg PA. Estimation of respiratory volumes from the photoplethysmographic signal. Part 2: A model study. Med Biol Eng Comput. Jan. 1999;37(1): pp. 48-53.

Foo JY, Wilson SJ. Estimation of breathing interval from the photoplethysmographic signals in children. Physiol Meas. Dec. 2005;26(6): pp. 1049-1058. Epub Oct. 31, 2005.

Johansson A. Neural network for photoplethysmographic respiratory rate monitoring. Med Biol Eng Comput. May 2003;41(3): pp. 242-248.

Farre R, Montserrat JM, Navajas D. Noninvasive monitoring of respiratory mechanics during sleep. Eur Respir J. Dec. 2004;24(6): pp. 1052-1060.

Johansson A, Stromberg T. Influence of tidal volume And thoracoabdominal separation on the respiratory induced variation of the photoplethysmogram. J Clin Monit Comput. 2000;16(8): pp. 575-581.

Shepard JW Jr, Pevernagie DA, Stanson AW, Daniels BK, Sheedy PF. Effects of changes in central venous pressure on upper airway size in patients with obstructive sleep apnea. Am J Respir Crit Care Med. Jan. 1996;153(1): pp. 250-254.

Kushida C, Giacomini A, Lee M, Guilleminault C, Dement W. Technical protocol for the use of esophageal manometry in the diagnosis of sleep-related breathing disorders. Sleep Med 3(2002) pp. 163-173.

Mannheimer P, O'Neil M, Konecny E. The influence of large subcutaneous blood vessels on pulse oximetry. J Clin Monitor Comput 18: pp. 179-188, 2004.

Foo J, Wilson S, Bradley A, Williams G, Harris M, Cooper D. Use of pulse transit time to distinguish respiratory events from tidal breathing in sleeping children. Chest 2005; 128; pp. 3013-3019.

Pitson D, Stradling J. Value of beat-to-beat blood pressure changes, detected by pulse transit time, in the management of obstructive sleep apnea/hypopnea syndrome. Eur Respir J 1998:12: pp. 685-692.

Argod J, Pepin J, Smith R, Levy P. Comparison of Esophageal Pressure with Pulse Transit Time as a measure of respiratory effort for scoring obstructive nonapneic respiratory events. Am J Respir Crit Care Med vol. 162 (2000) pp. 87-93.

Gisolf J, Van Lieshout J, Van Heusden K, Pott F, Stok W, Karemaker J. Human cerebral venous outflow pathway depends on posture and central venous pressure. J Physiol 560.1 (2004), pp. 317-327.

D Pilcher, C Scheinkestel, G Snell, A Davey-Quinn, M Bailey, T Williams. J Thorac High central venous pressure is associated with prolonged mechanical ventilation and increased mortality after lung transplantation. Cardiovasc Surg. 2005;129(4): pp. 912-918.

International Search Report/Written Opinion issued in PCTUS2007071242 on Mar. 13, 2008, 11 pages.

Smith M. (2008). Monitoring intracranial pressure in traumatic brain injury. Anesthesia and Analgesia 106: pp. 240-248.

The Brain Trauma Foundation. (2007). The American Association of Neurological Surgeons. The Joint Section on Neurotrauma and Critical Care. Intracranial pressure thresholds. Journal of Neurotrauma 24: pp. S55-S58.

Munch E, Weigel R, Schmiedek P, Schurer L. (1998). The Camino intracranial pressure device in clinical practice: reliability, handling characteristics and complications. Acta Neurochirurgica (Wien) 140: pp. 1113-1119.

Fernandes HM, Bingham K, Chambers IR, Mendelow AD. (1998). Abstract of Clinical evaluation of the Codman microsensor intracranial pressure monitoring system. Acta Neurochirurgica (Supplement), 1 page.

Citerio G, Andrews PJ. (2004). Intracranial pressure. Part two: clinical applications and technology. Intensive Care Medicine 30: pp. 1882-1885.

Shimbles S, Dodd C, Banister K, et al. (2005). Clinical comparison of tympanic membrane displacement with invasive ICP measurements. Physiological Measurement 26: pp. 1085-1092.

Petkus V, Ragauskas A, Jurkonois R. (2002). Abstract of Investigation of intracranial media ultrasonic monitoring model. Ultrasonics 40:829-833, 1 page abstract submitted.

Blaivas M, Theodoro D, Slerzenski PR. (2003). Elevated intracranial pressure detected by bedside emegency ultrasonography of the optic nerve sheath. Academic Emergency Medicine 10(4): pp. 376-381.

Firsching, R, Schutze R, Motschmann M, Behrens-Baumann W. (2000). Venous opthalmodyamometry: a noninvasive method for assessment of intracranial pressure. Journal of Neurosurgery 93 (1): pp. 33-36,29.

Schmidt B, Czosnyka M, Raabe A et al. (2003). Adaptive noninvasive assessment of intracranial pressure and cerebral autoregulation. Stroke 34: pp. 84-89.

Ursino M, Di Giammarco P. (1991). A mathematical model of the relationship between cerebral blood volume and intracranial pressure changes: the generation of plateau waves. Annals of Biomedical Engineering 19: 1 pp. 5-42.

Ursino M. (1988). A mathematical study of human intracranial hydrodynamics. Part I: the cerebrospinal fluid pressure. Annals of Biomedical Engineering 16: pp. 379-401.

Ursino M. (1988). A mathematical study of human intracranial hydrodynamics. Part II: simulation of clinical tests. Annals of Biomedical Engineering 16: pp. 403-416.

Popovic D, King C, Guerrero M et al. (2008). Validation of forehead venous pressure as a measure of respiratory effort for the diagnosis of sleep apnea. Accepted to Journal of Clinical Monitoring and Computing. Journal of Clinical Monitorint and Computing (2009) 23: pp. 1-10.

Vegfors M, Ugnell H, Hok B, et al. Experimental evaluation of two new sensors for respiratory rate monitoring. Physiological Measurement 1993; 14: pp. 171-181.

Johansson A, Oberg PA , Sedin G. Monitoring of heart and respiratory rates in newborn infants using a new photoplethysmographic technique. Journal of Clinical Monitoring 1999; 15: pp. 461-467.

Elwell CE, Owen_Reece H. Wyatt JS et al. (1996). Influence of respiration and changes in expiratory pressure on cerebral haemoglobin concentration measured by near infrared spectroscopy. Journal of Cerebral Blood Flow and Metabolism 16(2): pp. 353-357.

Czosnyka M, Czosnyka Z, Momjian S. Pickard JD. (2004). Cerebrospinal fluid dynamics. Physiological Measurement 25: pp. R51-R76.

Caricato A. Conti G, Della Corte F, et al. (2005). Effects of positive end-expiratory pressure (PEEP) on the intracranial system of patients with head injury and subarachnoid hemorrhage: the role of respiratory compliance. Journal of Trauma 58(3): pp. 571-576.

Huynh T, Messer M, Sing RF, et al. (2002). Positive end-expiratory pressure alters intracranial and cerebral perfusion pressure in severe traumatic brain injury. Journal of Trauma 53(3): pp. 488-492.

Lodrini S, Montolivo M, Pluchino F, Borroni V. (1989). Positive end-expiratory pressure in supine and sitting positions: its effect on intrathoracic and intracranial pressures. Neurosurgery24(6): pp. 873-877.

Lars-Owe, D. Koskinen. Clinical Experience with the Intraparenchymal Intracranial Pressure Monitoring Codman Microsensor System, Neurosurgery, vol. 56, No. 4, Apr. 2005, pp. 693-698.

* cited by examiner

REG waveform.

Features of the REG:
A-peak amplitude
B-rise time to peak amplitude
C-cardiac cycle period
D-dicrotic notch
E-descending limb (dashed-atherosclerosis NIRS measurement with
one source-detector pair Typical setup for recordings
from human subjects Physiological fluctuations in NIRS measurements:
cardiac, respiratory and blood pressure oscillations
(Meyer waves) are clearly visible.

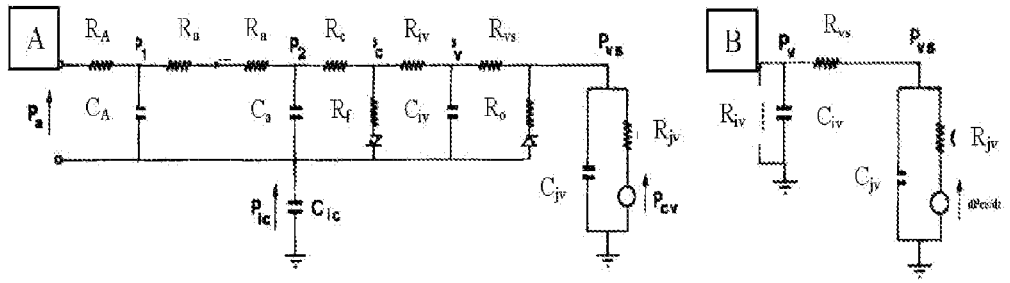
FIG. 4A          FIG. 4B
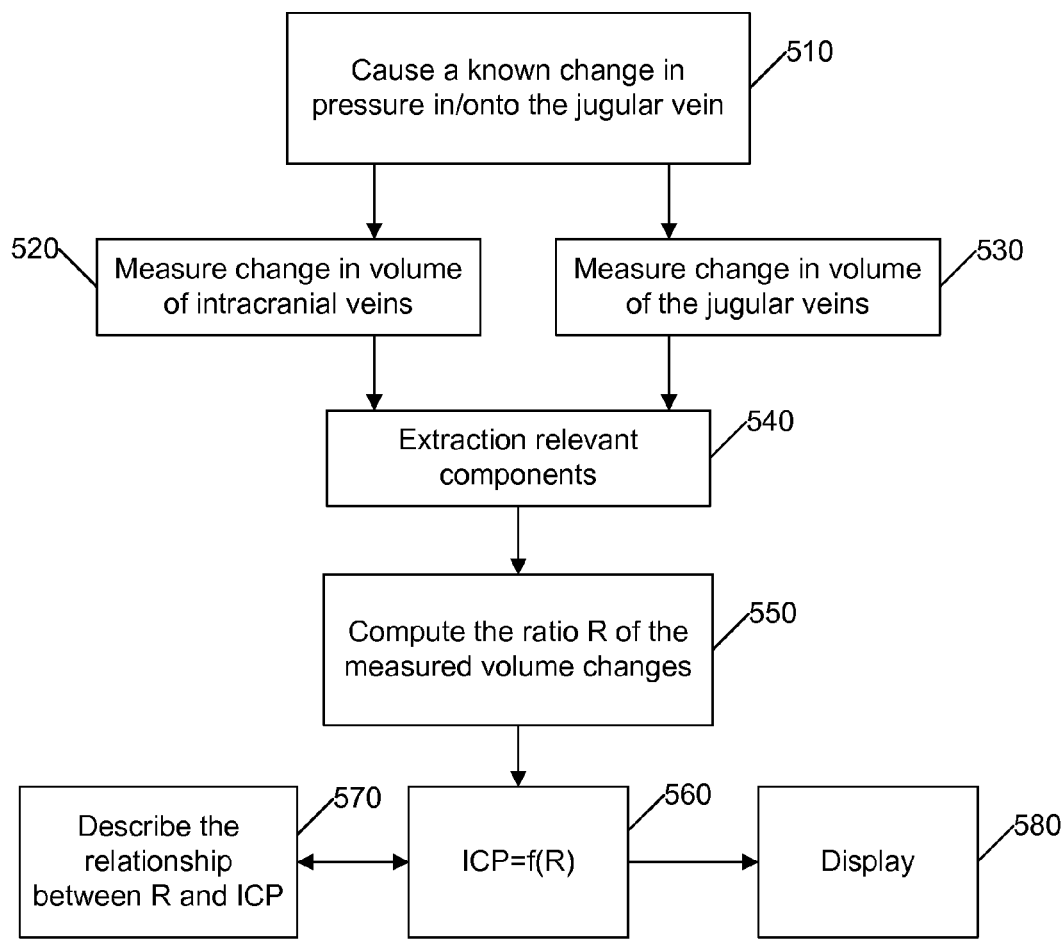
FIG. 5

METHOD AND APPARATUS FOR NON-INVASIVE ASSESSMENT OF HEMODYNAMIC AND FUNCTIONAL STATE OF THE BRAIN

RELATED APPLICATIONS

This application claims the benefit of U.S. Provisional Patent Application Ser. No. 61/149,850 filed Feb. 4, 2009, entitled "A METHOD AND APPARATUS FOR NON-INVASIVE MEASUREMENT OF INTRACRANIAL PRESSURE," which is hereby incorporated by reference in its entirety.

GOVERNMENT LICENSE RIGHTS

This invention was made with government support under contract #W81XWH-10-C-0061 awarded by Small Business Innovation Research, Office of the Secretary of Defense (SBIR/OSD). The government has certain rights in the invention.

BACKGROUND OF THE INVENTION

1. Field of the Invention

The present invention relates to the noninvasive assessment of the electrical and hemodynamic state of the brain. More particularly, the present invention relates to assessment by monitoring of intracranial pressure.

2. Description of the Related Art

Traumatic brain injury (TBI) is among the leading causes of death and disability in the US, with more than 1.4 million new incidents every year, leading to 235,000 hospitalizations and 50,000 deaths and attributing to $60 billion in direct and indirect medical costs. Moreover, it is estimated that over 5 million Americans have a permanent disability as a consequence of TBI. Clinical presentation and ultimate consequences of TBI are variable and dependent on the severity, extent, and localization of the injury, as well as on the promptness and adequacy of the care provided to the injured. Three conditions, often occurring in concert, are identified as particularly detrimental: silent (non-convulsive) seizures, decreased cerebral blood flow (ischemia), and increased intracranial pressure.

Silent Seizures:

Non-convulsive (or silent) seizures refer to epileptic attacks that do not involve the motor cortex, and subsequently do not result in muscle activity (as opposed to convulsive seizures, that manifest in twitches, cramps, prolonged (tonic) muscle contractions or the like). Silent seizures have been documented to occur frequently after traumatic or a variety of hemorrhagic injuries to the brain. The incidence of silent seizures increases as a function of the severity of injury, and other selected features of the injury such as the presence of hemorrhagic contusions. In recent years it has been convincingly demonstrated that non-convulsive seizures adversely affect the prognosis after brain insults by increasing the metabolic demands of the brain in a situation when cerebral blood flow is usually already compromised. While the treatment of silent seizures (with standard anti-epileptic drugs) is rather efficient, their detection remains the weakest point in the acute care of patients; they are impossible to detect upon standard clinical examination, and can only be revealed if the electrical activity of the brain is recorded (e.g., using an electroencephalographic (EEG) recorder). EEG is however infrequently recorded in most neuro-intensive care units because of the difficulties in using relatively bulky EEG systems in a crowded setting of an ICU, and in maintaining good electrical contact between the EEG electrodes and the scalp of the patient over longer periods of time.

Silent seizures can be detected from the continuously recorded EEG by either displaying the EEG signal to a trained human expert (typically a neurologist) or by submitting the recorded EEG signal to signal processing algorithms and/or classifiers designed to recognize and extract features (e.g. spikes, spike-and-wave complexes) indicative of an ongoing epileptic seizure. The first approach is essentially the only one used in the clinical practice, and it belongs to the public domain. The second approach is still largely limited to experimental settings, but with further improvements in computational technologies and artificial intelligence it may find its way to clinicians. Methods for automated detection of seizures have been disclosed in various patents, with some methods assuming the use of a portable EEG recording device and other methods assuming that any EEG recording device or system can be used for patient monitoring.

Cerebral Blood Flow and Detection of Ischemia:

Cerebral blood flow (CBF) is frequently compromised following a traumatic brain injury (TBI) due to a variety of reasons: direct damage to intracranial blood vessels, hypotension caused by concomitant hemorrhage, vasospasm caused by vasoactive substances released from the damaged brain tissue, or increased intracranial pressure (ICP). Decreased CBF can cause a secondary, ischemic brain injury, that is often more severe and extensive than the primary injury inflicted in an accident. However, standard methods for measuring CBF are technically complex, financially costly, and are applied in specialized institutions where the equipment and knowledge are available. See Table 1. Some of the methods from Table 1 belong to the public domain and some are disclosed in various patents. For example, in some patents, CBF is estimated from ultrasound measurements. In other patents, CBF is derived from near-infrared spectroscopy (NIRS) measurements after administration of an intravascular contrast (dye). In still other patents, a combination of EEG, rheoencephalography (REG) and peripheral physiological signals (such as EKG and pulse oximetry) can be used to estimate the cerebral blood flow and differentiate patients with atherosclerosis from healthy individuals. However, these methods are focused on only measuring the flow through the arterial portion of the cerebral vasculature.

TABLE 1

Methods for measurement of CBF

| Methods | Shortcommings for in-field use |
|---|---|
| Nitrous oxide inhalation method | Cumbersome, unsuitable for dynamic changes |
| O215 positron emission tomography (PET) | Radioactive, expensive, not portable |
| Single photon emission tomography (SPECT) | Radioactive, expensive, not portable |
| Perfusion-weighted MRI | Expensive, not portable |
| Xe-enhanced computerized tomography (CT) | Radioactive, expensive, not portable |
| Transcranial Doppler (TCD) | Considerable expertise required |
| Intracranial probes (based on laser flowmetry) | Invasive, risk of infections, not absolute measurement |

In accordance with principles of the present invention, the methods disclosed herein teach the use of rheoencephalography (REG) and optical measurements (e.g., near-infrared spectroscopy) for the assessment of cerebral blood flow and blood volume in the arterial and venous portion of the cerebral vasculature.

REG denotes a measurement of the electrical impedance of the head to the passage of an alternating current of low amplitude (~2 mApp) and relatively high frequency (~20-150 kHz). As blood is a much better conductor of electricity at these frequencies than most other tissues that compose the head, the measured impedance varies with the pulsatile flow of blood. See FIG. 1A. Changes in the morphology of the REG waveform such as the peak amplitude, rise time to peak amplitude, and appearance of the descending limb have been shown to reflect changes in cerebral blood volume and flow in a variety of conditions including experimental hemorrhage, post-traumatic contusions, cerebral atherosclerosis, and other cerebral vasculopathies. See FIG. 1B.

Near-infrared spectroscopy (NIRS) refers to a measurement in which light at wavelengths 760-1400 nm (near-infrared range) is delivered to a body part at one point, and the amount of light that is transmitted through the body part is measured with a light sensor located at another point at some distance from the point where the light emitter is located. See FIG. 2A. In cases where the brain is an object of the measurements, several light emitters and sensors organized into a grid are typically utilized. See FIG. 2B.

Although the light is to some extent absorbed by all tissues lying on its path (e.g., skin, bone, cerebrospinal fluid, brain tissue, blood), the absorption caused by blood can be easily separated from the other tissues due to its pulsatile nature. For example, three types of pulsations can be found in the raw NIRS signal: arterial pulsations synchronous with cardiac cycles (typical frequency: 40-200 per minute), venous pulsations synchronous with respiration (typical frequency: 8-20 per minute), and so-called "Meyer oscillations" that are synchronous with slow blood pressure changes caused by sympathetic stimulation (typical frequency: less than 5 per minute). Clinical applications of the NIRS have so far focused mostly on the arterial pulsations, utilizing their amplitude to derive cerebral tissue oxygenation, cerebral blood volume and blood flow, or detect intracranial hematomas and brain edema. Recently, however, venous pulsations in the NIRS signal have been used to measure cerebral venous oxygenation in neonates and adults.

In comparing the two methods (REG and NIRS) the following should be noted: while both NIRS and REG detect arterial pulsations, and are subsequently capable of monitoring cerebral blood volume and flow in the arterial portion of the vasculature, NIRS has an advantage of revealing information about the venous portion of the vascular bed. However, since the near-infrared light penetrates only 5-10 mm into the head, NIRS can only monitor blood flow in the brain cortex but not in the deeper structures. REG on the other head does not make a distinction between the cortex and deeper structures as both have similar electrical conductance.

Intracranial Pressure:

Intracranial pressure (ICP), or the pressure inside of the skull, is usually altered following a traumatic brain injury or hemorrhagic insult, as these conditions lead to volume expansion in a rigid and non-expandable skull (due to blood collections inside of the skull, or brain edema, etc.). Once ICP increases over 20 mHg a vicious cycle easily develops in which the increased ICP decreases cerebral blood flow, leading to brain tissue ischemia that results in edema, which through a volume expansion further increases ICP. The ultimate effect is a severe decrease in cerebral blood flow (CBF) with consequent brain tissue hypoxia and death of affected neurons. Consequently, monitoring of the ICP and preventing its increase are fundamental in treatment of conditions such as traumatic brain injury, stroke, and spontaneous intracranial hemorrhage.

The gold standard technique for ICP monitoring is an invasive procedure that involves inserting a fluid-filled catheter into the intracranial compartment, and connecting it to a standard pressure transducer. Alternatively, micro-transducer-tipped ICP probes can be inserted in the brain parenchyma or subdural space through a skull bolt or small burr hole. Other methods such as subarachnoid and epidural transducers or spinal tap have much lower accuracy. However, the invasive methods for monitoring ICP share several common drawbacks: the transducers have to be calibrated before insertion; their output drifts, requiring either a recalibration or replacement of the catheter after 36-48 hours; insertion of a catheter carries a risk of brain or spinal cord damage and infection; and the placement of a catheter requires a highly trained individual, such as a neurosurgeon. For these reasons, invasive ICP monitoring techniques cannot be used outside of the hospital setting.

Non-invasive methods of measuring ICP are disclosed in Popovic et al., "Noninvasive Monitoring of Intracranial Pressure," Recent Patents on Biomedical Engineering 2(3):1-15 (2009). Table 2, shown below, is reproduced from U.S. Pat. No. 5,617,873, US20016231509, US20026413227, U.S. Pat. No. 4,984,567, U.S. Pat. No. 4,971,061, WO00068647, U.S. Pat. No. 5,919,144, U.S. Pat. No. 5,388,583, US20026457147, US20046761695, U.S. Pat. No. 5,993,398, US20006086533, US20067104958, U.S. Pat. No. 5,951,477, U.S. Pat. No. 5,074,310, U.S. Pat. No. 5,117,835, US20006117089, US20046746410, US20046740048, US20046773407, U.S. Pat. No. 5,993,398, U.S. Pat. No. 4,564,022, U.S. Pat. No. 4,841,986, US20067147605, US20036589189, WO98034536, US20026390989, US20067122007, US20060206037, and U.S. Pat. No. 4,204,547, herein incorporated by reference.

TABLE 2

Comparison of methods for noninvasive monitoring of ICP

| Method | Accuracy (SE of measurement) | Skill level required for use | Cost of technology | Continuous monitoring | Other advantages or shortcomings |
|---|---|---|---|---|---|
| Ultrasound time of flight | ±10 mmHg | Low | Moderate | Yes | Easily portable and field-deployable |
| Transcranial Doppler | ±10 mmHg | Expert | Moderate | No | Finding correct vessels difficult even for experts |
| Acoustic properties of cranial bones | Not validated | Low | Low / moderate | Possible | Easily portable and field-deployable |

TABLE 2-continued

Comparison of methods for noninvasive monitoring of ICP

| Method | Accuracy (SE of measurement) | Skill level required for use | Cost of technology | Continuous monitoring | Other advantages or shortcomings |
|---|---|---|---|---|---|
| EEG | Not validated | Moderate | Moderate | No | Repeated visual stimulation needed Cumbersome |
| MRI | Not validated | Expert | High | No | Not a bedside assessment |
| Tympanic membrane displacement | ±10-15 mmHg | Moderate | Low | No | Inapplicable in older patients |
| Otoacoustic emission | ±10-15 mmHg | Moderate | Low | No | Inapplicable in older patients |
| ONSD | ±5-10 mmHg | Moderate/High | Moderate | No | |
| Ophthalmo-dynamometry | ±2-3 mmHg | Expert | Low | No | Cumbersome |
| Jugular blood flow velocity measurement | Not validated | Expert | Low / moderate | No | Cumbersome Unpleasant |

Table 2 illustrates that the non-invasive methods' common drawback is insufficient accuracy: the margins of error of ICP estimates are of the same order of magnitude as the whole range of ICP that is clinically of interest (0-50 mmHg). The noninvasive methods can therefore reliably identify only subjects with low to normal or very high ICP, but not the clinically most important population with moderately increased ICP (15-30 mmHg).

The present invention seeks to overcome the deficiencies described above.

SUMMARY OF THE INVENTION

A method and apparatus for noninvasive assessment of the hemodynamic state of the brain is described herein. In some embodiments, the method and apparatus further provide information about the presence of silent seizures, magnitude and regional distribution of cerebral blood flow, and absolute value of intracranial pressure (ICP).

In accordance with an aspect of the invention, a method for determining a change of intracranial pressure in a patient includes: (1) measuring a patient's electroencephalographic (EEG), rheoencephalographic (REG) and optical signals from the surface of the head; (2) acquiring non-cranial physiological signals from the same patient such as EKG; (3) application of standard signal conditioning procedures and digitization of acquired signals; (4) extraction of various features from the acquired signals; (5) comparison the extracted features either to a set of pre-defined thresholds or to a database of the same features derived from a representative sample of patients and healthy individuals; and (6) detection of silent seizures and other conditions of interest, and measurement of cerebral blood flow, intracranial pressure, and other variables of interest, on the basis of the aforesaid comparisons. Embodiments are also described that include a portable device that combines the electric (EEG and REG) and optical methods (near infrared optical spectroscopy-NIRS or pulse oximetry).

The foregoing and other features and advantages of the present invention will be apparent from the following more detailed description of the particular embodiments of the invention, as illustrated in the accompanying drawings.

BRIEF DESCRIPTION OF THE FIGURES

FIG. 4A represents an exemplary electrical model of intracranial hemodynamic used to derive the relationship between the ratio (R) and intracranial pressure (ICP);

FIG. 4B represents a small-signal simplification of the electrical model of FIG. 4A; and FIG. 5 represents a block diagram of a method in accordance with an embodiment of the present invention.

DETAILED DESCRIPTION OF THE INVENTION

After reading this description, it will become apparent to one skilled in the art how to implement the invention in various alternative embodiments and alternative applications. The following description sets forth numerous specific details, such as examples of specific systems, components and methods in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Particular implementations may vary from these exemplary details and still be contemplated to be within the spirit and scope of the present invention.

Figure 1A:
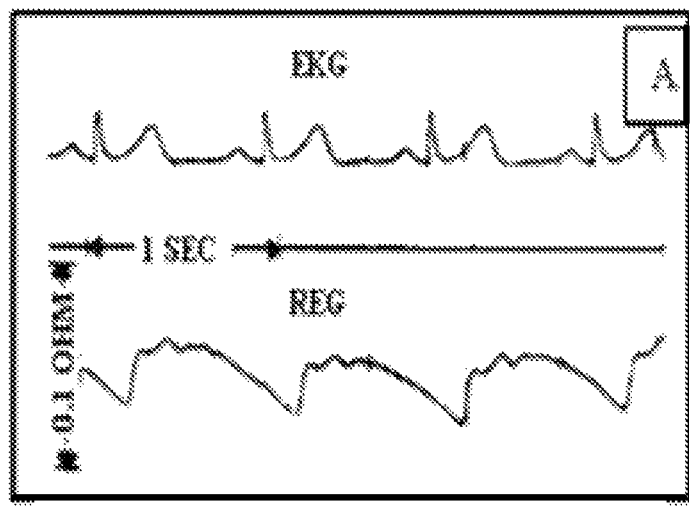
FIG. 1A represents a graph illustrating an exemplary REG waveform.
Figure 1B:
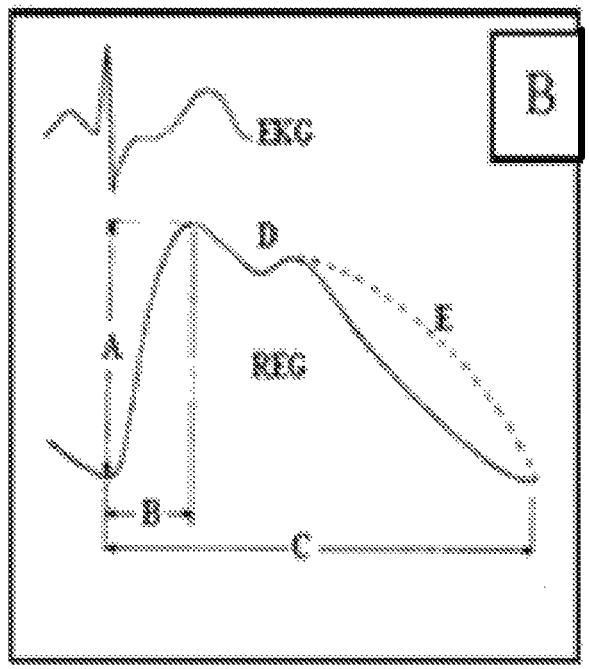
FIG. 1B represents a graph illustrating features of the exemplary REG waveform of FIG. 1A.
Figure 2A:
FIG. 2A represents a schematic drawing of an NIRS measurement with one source-detector pair.
Figure 2B:
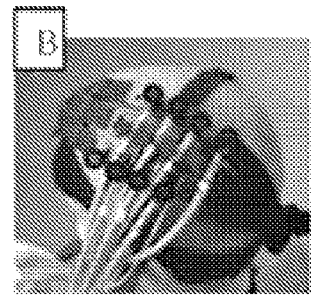
FIG. 2B represents a schematic drawing of the typical setup for NIRS recordings for human subjects.
Figure 2C:
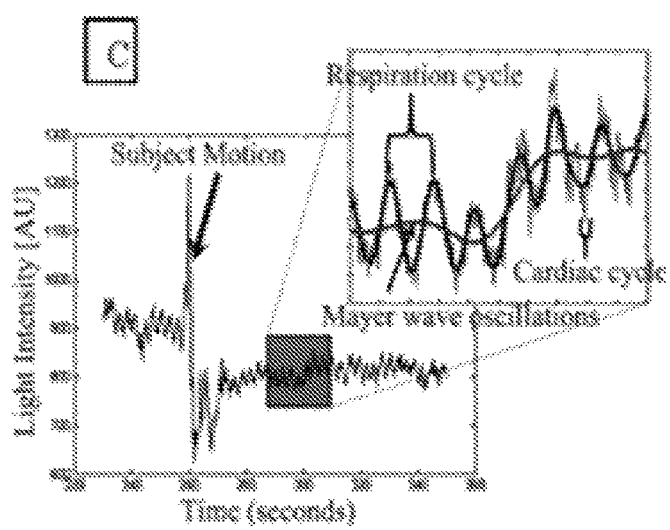
FIG. 2C represents a graph illustrating exemplary physiological fluctuations in NIRS measurements.
Figure 3:
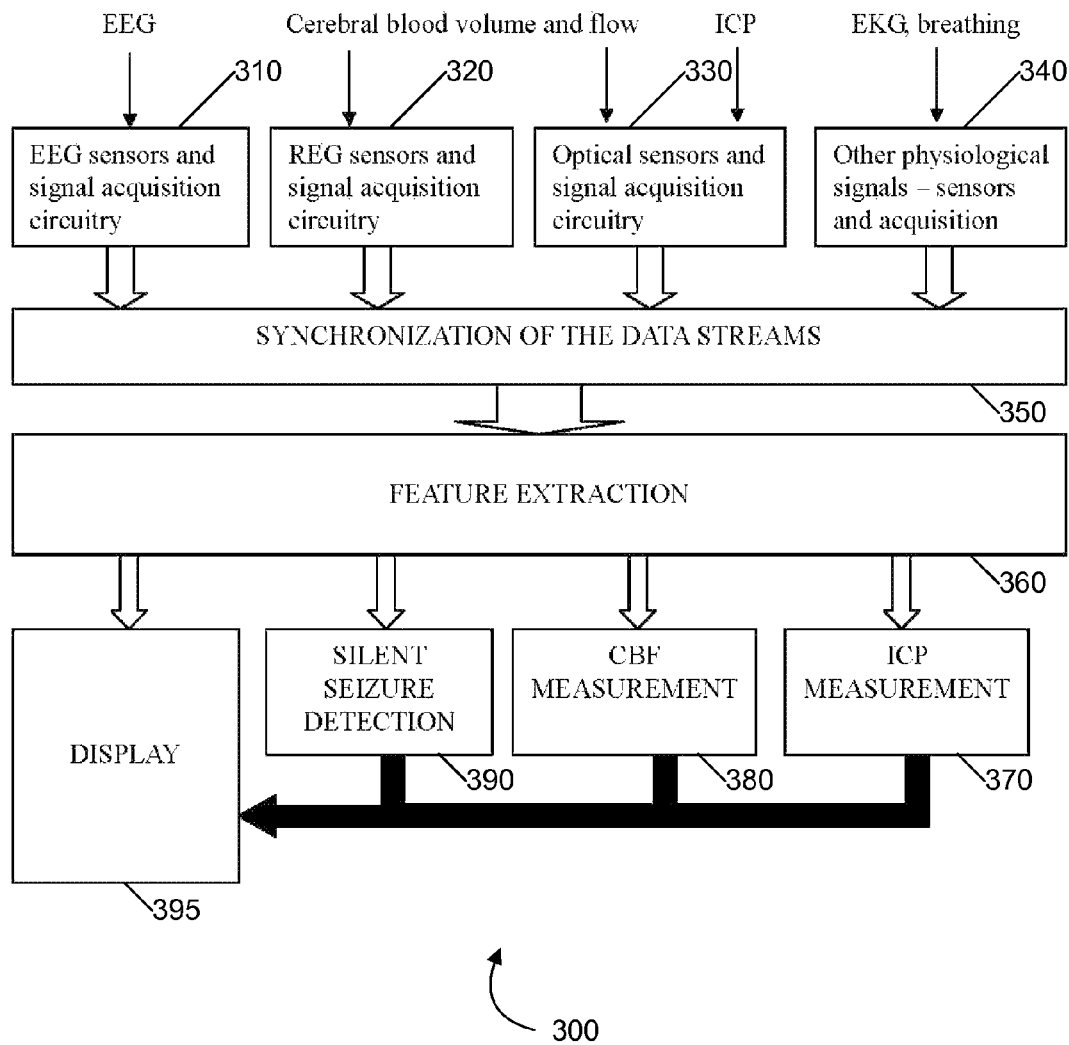
FIG. 3 represents a block diagram of an apparatus in accordance with an embodiment of the present invention.

Referring now to FIG. 3, a block diagram representing a system 300 in accordance with an embodiment of the present invention is shown. In one embodiment, the electrical activity of the brain (e.g., electroencephalogram (EEG)) (block 310) is acquired continuously and simultaneously with rheoencephalographic (REG) (block 320) and optical measurements (block 330) that carry the information about the blood flow through the brain and the value of intracranial. Blocks 310, 320, 330 represent an EEG module, an REG module and an optical module, respectively, each having an associated sensor. Examples of the sensors are described below. In one embodiment, each of these modules includes signal conditioning circuitry appropriate for the sensor being used. Block 340 represents a physiological module, having an associated sensor and related circuitry, the sensor described below. In some embodiments, physiological signals (block 340) may be acquired from parts of the body other than the brain and/or head, such as for example electrocardiogram (EKG), respiration, or tissue oxygenation measured with pulse oximetry.

The EEG may be acquired with two or more electrodes positioned on the scalp of the patient. In one embodiment, the EEG is recorded using a headset and portable wireless acquisition device, such as described in U.S. Pat. No. 6,161,030, and U.S. Pat. No. 6,381,481 B1, incorporated herein by reference. In an embodiment, the headset communicates with, and transmits the acquired physiological signals to, a personal computer in a wireless manner to reduce signal contamination. However, those skilled in the art will recognize that any standard EEG acquisition system (e.g., wireless or wired, portable or laboratory) could be used for the same purpose utilizing any of the available EEG electrodes (e.g., passive 'wet' electrodes with conductive gel or paste; passive 'dry' electrodes (no conductive gel or paste); or active electrodes (e.g., with an on-site signal amplification)).

The REG signal may acquired using two or more electrodes positioned anywhere on the scalp of the patient. A sinusoidal current of arbitrary frequency and small enough amplitude to not cause harm (e.g., <5 mApp) may be constantly delivered through the electrodes. The voltage oscillations elicited may be recorded from the same or different electrodes located nearby those that deliver the current.

As explained above, the ratio of the recorded voltage amplitude to the amplitude of the delivered current (e.g., electrical impedance between the electrodes) is a function of the arterial blood flow through the regions of the brain located along the path of the current. In one embodiment, the amplitude of the current is approximately 1-2 mApp, the frequency of the current is approximately between 20-50 kHz, the same electrodes are used for the acquisition of the EEG and REG signals, and a portable headset that transmits the data wirelessly to a personal computer is used for the acquisition. However, those skilled in the art will recognize that any device or system capable of delivering a sinusoidal current through a pair of electrodes and simultaneously acquiring the voltage fluctuations from the same or a different pair of electrodes, whether it be portable and wireless or not, can be used for the same purpose. Additionally, in some embodiments, the impedance calculated from the REG signal can be utilized as an indicator of the contact between the electrodes and the scalp.

The acquisition of the optical signal (block 330) may be achieved by at least one light source and one light sensor located on the scalp at some distance from each other. In one embodiment, a plurality of light sources (e.g., LEDs or laser sources connected to optic fibers) and light sensors (e.g., photodiodes) are organized in a grid. Preferably the light source emits and the light sensors register light of wavelength between 760-1400 nm, similar to standard NIRS systems. In a preferred embodiment, the light sources and sensors are integrated into the portable, wireless headset that contains the EEG/REG electrodes. However, those skilled in the art will recognize that any light source of a suitable shape (so that it can be applied on the head), emitting light of arbitrary wavelength, and any light detector can be used for the same purpose. Those skilled in the art will recognize that the choice of the number, type and configuration of light sources and light detectors is subject to various engineering considerations such as ensuring the proper contact between the sources/detectors and the skin, ensuring desired paths of the light, achieving high signal-to-noise ratio, enabling low-power or portable implementations, and the like, and that therefore the aforesaid examples do not limit the scope of the present invention but represent only some of the multitude of possible realizations.

The acquisition of other physiological signals (block 340) such as the EKG, respiration or tissue oxygenation may be accomplished using a variety of standard sensors (e.g., EKG electrodes, inductive respiratory bands, pulse oximeters). In a preferred embodiment, these sensors are connected to an autonomous portable data acquisition unit, worn on the belt or attached elsewhere on the body so to be comfortable and easy to use, that performs the analog signal processing, digitizes the signals, and transmits the digitized data wirelessly to a personal computer. Yet, in another preferred embodiment, a wireless portable data acquisition device is used for the acquisition of peripheral physiological signals and signals from the head (EEG, REG and optical signals). Those skilled in the art will however recognize that appropriate sensors can be connected to any data acquisition system (portable or in-lab, wireless or wired) for the purpose of the acquisition of these peripheral signals as long as the data stream from the system can be synchronized in real-time with the data stream from the data acquisition system used to record the EEG, REG and optical signals from the head (block 350).

Synchronization of the data streams (block 350) can be achieved in several ways, (e.g., via a synchronization module) depending on the configuration of the sensors and data acquisition units used for the signal recording. In one embodiment, the sensors (e.g., EEG electrodes/headset, REG electrodes/headset, light sources and detectors, EKG electrodes, respiratory bands, pulse oximeter and/or other peripheral sensors) are connected to a single data acquisition device, and some or all of the incoming signals receive upon digitization a time stamp from a single processor or microcontroller unit that operates in the data acquisition device. This data acquisition device may then transmit the data with the time stamps to feature extraction block 360, via a wireless link, through a wired connection such as RS232, or via a network TCP/IP protocol.

In another embodiment, a plurality of data acquisition units are used, some worn on the head and acquiring the EEG, REG and/or optical signals and some worn elsewhere on the body and acquiring physiological signals from sensors such as EKG electrodes, respiratory bands, or pulse oximeters. In this embodiment, the plurality of data acquisition units transmit the data wirelessly to a single unit, which assigns time stamps to data packets upon their receipt, thereby accomplishing the synchronization. Physically, this unit can be realized as a microcontroller with a real-time clock and an antenna attached to it, or as a personal computer or a personal device assistant (PDA) with a wireless link. Those skilled in the art will recognize that the exact implementation of the synchronization unit is not crucial for, and by no means limits the scope of, the present invention.

Feature extraction block 360 performs various mathematical operations on the digitized EEG, REG, optical and other peripheral physiological signals in order to derive variables that are related to, or indicative of, epileptic seizures, comatose state(s) including the state of brain death, cerebral blood flow, cerebral blood volume, and/or intracranial pressure. In some embodiments, feature extraction block 360 performs the operations in real-time. Such features, and mathematical operations required for derivation thereof, include but are not limited to the following:

1) Low-, high-, band-pass and/or band-stop filtering of the row signals with a variety of digital filters, such as linear FIR filters, IIR filters, adaptive filters, or non-linear filters based on the higher-order statistics (HOS filters). For example, EEG may be filtered with a 50/60 Hz notch filter and a band-pass filter (e.g. 0.5-32 Hz) to remove possible artifacts due to e.g., eye movements or electrical activity of the facial and neck muscles (EMG); pulsatile REG signal may be filtered with a band-pass filter (e.g. 0.1 Hz-5 Hz, corresponding to a heart rate from ~10 bpm to 300 bpm); the optical signals may be filtered with a filter bank consisting of 3 filters: a low-pass filter with cutoff at or around 0.05 Hz (to extract Meyer oscillations), a band-pass with a lower cutoff at or around 0.1 Hz and an upper cutoff at or around 0.4 Hz (to extract venous pulsations) and a band-pass filter with a lower cutoff at or around 0.4 Hz and an upper cutoff at or around 5 Hz (to extract arterial pulsations); EKG may be filtered with a 50/60 Hz notch filter and a band-pass filter (0.5 Hz-32 Hz) to eliminate the power line interference and spurious muscle activity that contaminates the signal; respiration may be filtered with a band-pass filter (0.05-0.5 Hz). Those skilled in the art will recognize that the exact choice of filters is dependent on factors such as characteristics of the signal of interest and of sensor(s) with which it has been recorded, and subject to various engineering considerations such as achieving an optimal signal-to-noise ratio, and that therefore it by no means limits the scope of the present invention.

2) Spectral analysis of the acquired EEG, REG, optical and other physiological signals recorded from one or more scalp locations, or from elsewhere on the body. Power spectral density (PSD) may be computed using standard non-parametric algorithms (e.g., Fast Fourier Transform, filter banks, and so forth) or parametric techniques such as auto-regressive (AR) models or autoregressive moving-average (ARMA) models. In an embodiment, PSD indices are computed on a second-by-second basis for the range of frequencies from 1 to 50 Hz in 1 Hz steps, and further grouped or summed into the conventional bands known in the art, namely delta (1-4 Hz), theta (4-7 Hz), alpha (8-13 Hz), beta (13-30 Hz) and gamma (30-50 Hz). Those skilled in the art will recognize that the exact implementation of the spectral analysis of the acquired signals is subject to various engineering considerations, including the desired precision and speed of the computation, and that therefore does not limit the scope of the present invention.

3) A number of spectral indices derived for all or some of the acquired signals from the power spectral indices calculated as described above, such as central and edge frequencies, bandwidth, and spectral entropy (SEN) of the signal.

4) A number of time-domain features may be calculated on all or some of the acquired signals, such as: standard deviation, Hjorth parameters (signal mobility and complexity) or Barlow parameters.

5) A number of non-linear measures such as: correlation dimension (D2), Lyapunov exponents or Kolmogorov's entropy.

6) Peak amplitude, rise time to peak amplitude and slope of the descending limb of the pulsatile waveform of the REG signal. As explained above, these features are related to (arterial) cerebral blood flow.

7) Peak amplitude, rise time to peak amplitude and slope of the descending limb of the pulsatile waveform of each of the three components of the optical signal: arterial pulsations, venous pulsations and Meyer waves. As explained above, these features are related to blood flow and oxygen saturation in the arterial and venous portion of the cerebral vasculature respectively; and Meyer oscillations provide information about sympathetic activity in the cerebral vascular bed. Furthermore, venous pulsations may be used to derive an absolute value of intracranial pressure (ICP).

8) Integral, over a variable period of time, of the variables from 6 and 7. Such integral is commensurate to the overall blood volume in the corresponding compartment (e.g., the integral of the amplitudes of arterial pulsations is commensurate to the blood volume in the cerebral arteries, while the integral of the amplitudes of venous pulsations is commensurate to the blood volume in the cerebral veins and dural sinuses). Changes in blood volume may be indicative of cerebral edema (brain swelling).

9) Ratios of variables derived as described in 1-8.

10) Ratios of variables derived as described in 1-8 between different locations on the scalp and/or body.

11) Measures of time series interdependency such as covariance, correlation, coherence or mutual information (MI) between different signals, or different locations on the scalp or body.

12) Weighted linear composites (e.g., linear combinations), or complex mathematical functions of the primary measures in 1-11.

The detection of silent seizures (block 390) may be accomplished by at least two ways. In one embodiment, a band-pass filtered EEG signal acquired at one or several locations on the scalp is presented in real-time to an expert (e.g., a neurologist) on a display 395, and the expert determines the presence of epileptic discharges and choice of treatment. In another embodiment, spikes and spike-and-wave complexes (which are indicative of epileptic seizures) are present in the acquired EEG signal, and are detected by a variety of linear and non-linear analytical methods, such as period-amplitude analysis, spectral analysis (as described above), entropy analysis in multidimensional space, chaotic time-series analysis, etc. Again, those skilled in the art will recognize that the exact choice of the method for detection of epileptic seizures is not crucial for, and does not limit the scope of, the present invention.

Cerebral blood flow (CBF) (block 380) may be determined from the REG or optical recordings by calculating any, some, or all features described in 1-12 above, and relating these features to CBF values measured with one of standard methods (e.g., Xe-enhanced computerized tomography) on a representative sample consisting of patients with TBI and healthy subjects. The relationship between the features (1-12) and CBF values measured with the standard method can be established in a form of a mathematical function (linear or non-linear), or in a form of a look-up table, or a combination thereof. In an embodiment, features described under 6 and 7 are utilized, and the relationship between these features and CBF values has a form of a multivariate regression equation. However, those skilled in the art will recognize that the exact choice of the features and form of relationship should not limit the scope of the present invention.

Intracranial pressure (ICP) (block 370) may be determined from the ratio of changes in the intracranial venous volume and changes in the volume of blood in the jugular vein. It is appreciated that changes in the amount of absorbed light are proportional to changes in the volume of blood. In some embodiments, the measurement of changes in volume of intracranial and jugular veins may be performed with non-invasive optical methods by determining, directly or indirectly, the amount of light absorbed by the venous blood in the intracranial compartments, or the jugular veins. A variety of light sources and light detectors may be used for the measurement. As an example, in one configuration a reflectance pulse oximeter is used on the neck while a near-infrared spectrometer (NIRS) is used on the skull. In another configuration, two NIRS spectrophotometers are used, one on the neck and one on the skull. In yet another configuration, custom-designed light sources (e.g. LED diodes, or optic fibers connected to a laser) and light detectors (e.g. photodiodes, or CCD sensors) are used at both locations.

Also, it is known that changes in ICP may cause pressure and/or volume changes in pressure/and or volume patterns in vessels such as veins. Consequently, ICP and/or changes in ICP can be determined through detecting and/or measuring changes in transmission of pressure of a vein. Such a method can include determining a baseline pressure (or volume) pattern of a vein (for example caused by normal breathing) and comparing the baseline pressure pattern of the vein with an actual pressure pattern of the vein in the patient. The baseline pressure pattern of the vein may be determined from a healthy patient or a pool of patients.

Since the surrounding structures of the jugular veins (e.g., air-filled trachea, carotid artery and large, dense muscles) differ in their physical and optical characteristics (e.g., length of the optical path, optical density, reflectance, etc.) from that of the skull (e.g., bone) the sources and detectors used on the head and neck may require different calibrations. Those skilled in the art will recognize that the choice of the number, type and configuration of light sources and light detectors is subject to various engineering considerations such as ensuring the proper contact between the sources/detectors and the skin, ensuring desired paths of the light, achieving high signal-to-noise ratio, enabling low-power or portable implementations, and the like, and that therefore the aforesaid examples do not limit the scope of the present invention but represent only some of the multitude of possible realizations. Furthermore, in some embodiments, blocks 350, 360, 370, 380, and 390 may each comprise modules and associated circuitry, and reside on one or more processors.

As described by Ursino et al., "A mathematical model of the relationship between cerebral blood volume and intracranial pressure changes: the generation of plateau waves," Annals of Biomedical Engineering 19:15-42 (1991), the resistance and compliance of the cerebral veins are a function of intracranial pressure:

$$C_{iv} = \frac{1}{K_v(P_v - P_{ic})} \quad (1)$$

$$R_{iv} = R_{iv}^0 \frac{(P_v - P_{cs})}{(P_v - P_{ic})}, \quad (2)$$

wherein $C_{iv}$ represents compliance and $R_{iv}$ resistance of the intracranial veins, $P_{ic}$ is intracranial pressure, $P_v$ is pressure inside the intracranial veins, $P_{cs}$ denotes pressure in the cavernous sinuses, $R^0_{iv}$ represents basal resistance of the intracranial veins under conditions of maximum dilation, and $K_v$ is elasticity constant of the intracranial veins.

The formula that describes the transmission of pressure changes originating in the jugular veins to intracranial veins will be now derived using the model of intracranial compartment developed by Ursino et al. and shown in FIG. 4A.

Turning to FIG. 4A, $R_A$, $R_a$, $R_c$, $R_{iv}$, $R_{vs}$, $R_{jv}$ represent resistances to blood flow of large arteries, arterioles, capillaries, intracranial veins, venous sinuses and jugular veins respectively, whereas $C_A$, $C_a$, $C_{iv}$, $C_{ic}$, $C_{jv}$ model compliance of large cerebral arteries, arterioles, intracranial veins, intracranial space filled with CSF and jugular veins, respectively. In an embodiment, the production and drainage of CSF is modeled with diodes (enforcing the unilateral flow) and resistors $R_f$ and $R_o$ representing resistances to CSF formation and CSF outflow, respectively. The model was able to successfully reproduce classical experimental and clinical findings such as the generation of the ICP pulse wave synchronous with heart beats, generation of ICP plateau waves and the results of several clinical maneuvers. As a result, the model is considered an accurate presentation of intracranial hemodynamic.

Because changes in intracranial venous pressure elicited by small changes in the jugular venous pressure are of interest, small-signal analysis can be applied to the original model, resulting in a simplification of the model. Using Kirchhoff's rules, the relation between the change in intracranial venous pressure ($dP_{iv}/dt$) and jugular venous pressure ($dP_{jv}/dt$) may be derived as follows:

$$\frac{\frac{dP_{iv}}{dt}}{\frac{dP_{jv}}{dt}} = \frac{1}{1+r}, \quad (3)$$

where $$r = \frac{R_{jv} + R_{vs} + j\omega C_{jv}R_{jv}R_{vs}}{R_{iv}} \times \frac{(1+j\omega C_{iv}R_{iv})}{(1+j\omega C_{jv}R_{jv})} = \quad (4)$$

$$\frac{F_{ind}(\omega)((1+j\omega C_{iv}R_{iv}))}{R_{iv}},$$

and ω is the radial frequency of the change of jugular venous pressure. In equation (4) the coefficient r is presented as a product of an ICP-independent component $F_{ind}(\omega)$ and an ICP-dependent factor containing ICP-dependent intracranial venous resistance and compliance described with equations (1) and (2).

In some embodiments, changes of pressure in the intracranial veins cannot be measured non-invasively, and are therefore not of direct use for this application. However, changes in pressure are related to changes in volume by simple relations:

$$\frac{dV_{iv}}{dt} = C_{iv} \times \frac{dP_v}{dt} \quad (5)$$

$$\frac{dV_{jv}}{dt} = C_{jv} \times \frac{dP_{jv}}{dt} \quad (6)$$

Combining equations (3)-(6), for the physiologically plausible values of $R_{iv}$ and $C_{iv}$ $|j\omega R_{iv}C_{iv}| \gg 1$ the following expression for the ratio between the changes in intra- and extracranial venous volume is:

$$R = \frac{\frac{dV_{iv}}{dt}}{\frac{dV_{jv}}{dt}} = \frac{1}{C_{jv}} \times \frac{C_{iv}}{1+j\omega F_{ind}(\omega)C_{iv}}. \quad (7)$$

The ratio R is therefore a non-linear function of the compliance of intracranial veins $C_{iv}$, which is a non-linear (e.g., hyperbolic) function of ICP. The ratio R therefore decreases with increasing ICP, and does not depend on the amplitude of the pressure change in the jugular veins ($d_{jv}/dt$).

Turning now to FIG. 5, a method 500 for non-invasive measurement of intracranial pressure, is shown. First, a known change in pressure in the jugular vein is introduced (block 510) while simultaneously the related changes in volume are measured of intracranial veins (block 520) and the jugular veins (block 530). In general, measured changes in volume will contain components that are not all related to the elicited change in pressure in the jugular veins. However, the components corresponding to the introduced pressure change may be isolated using the knowledge of the time course of the pressure changes introduced by block 510, and applying appropriate digital signal processing techniques. This extraction of relevant components is represented by block 540. The ratio R of the measured and relevant changes in volume of intracranial and the jugular veins is computed (block 550) and the corresponding value of intracranial pressure is derived (block 560). In some embodiments, the value of intracranial pressure is an absolute value. Function f that relates ICP to the ratio R can be described either empirically, by performing a series of the aforesaid measurements on animal or human subjects with known ICP and tabulating the computed R against the known ICP values, or analytically, by inverting equation (7) (block 570). Finally, the determined ICP value is displayed to the user (presumably a physician or a medic) at block 580 via a display element. The display element may be an LED display, an LCD display, a computer screen, etc.

In one embodiment, breathing, whether spontaneous or assisted, is used as a source of the pressure changes in the jugular vein. This jugular pressure profile can be obtained by monitoring respiration with e.g., a piezo-electric transducer attached to an elastic band wrapped around the chest, a respiratory inductive plethysmography (RIP), a nasal canula connected to a pressure sensor, a thermistor, a microphone, or with any other sensor or method that can detect breathing.

Alternatively, respiration need not be monitored. Since breathing results in relatively simple, nearly sinusoidal variations of the pressure with the main frequency in the range from 0.1-0.4 Hz (corresponding to approximately 6-24 breaths/minute), the relevant components of the measured volume changes can be separated out in block 550 blindly, by e.g., applying a digital band-pass filter with the aforesaid or a similar pass band; or by performing Fourier transform of the input signal and detecting the strongest peaks in the 0.1-0.4 Hz range. Those skilled in the art will recognize that any other signal processing approach that can isolate the breathing-related sinusoidal variations in the measured volume change signals may be used in block 540.

In one embodiment, once the relevant components have been extracted in block 540, the ratio R is computed by dividing the intensity of the component measured on the head/skull with the intensity of the component measured on the neck (block 550), which is followed by computing the corresponding value of intracranial pressure, e.g., by relying on Equation 7 (block 560).

The theoretical relationship between the ratio R and ICP, described analytically by Equation 7, may be practically implemented in at least two ways. One is to use the hemodynamic constants (resistances, compliances, elasticity constants, etc.) as determined in the art and analytically invert the equation so that it has a form of ICP=f(R), where f stands for a mathematical function. This solution is technically simple, but may not yield the most accurate results, because of the considerable between-subject variability of the hemodynamic constants, which means that the mean values from the art may not fit all well. Alternatively, the R-ICP relationship (heretofore and interchangeably 'curve') may be determined empirically, first on animal models where free manipulation of ICP is possible and then finely tuned on human subjects with increased ICP. The empirical relationship may then either be tabulated (e.g., presented as an ordered sequence of pairs—(R, ICP)—where each value of R corresponds to one value of ICP), or an analytical curve may be fit through the empirical sequence and subsequently used as a description of the R-ICP relationship. In some embodiments, block 570 is physically embodied in the same processor or in the accompanying memory elements where the tabulated relationship or the utilized hemodynamic constants are stored.

In an embodiment, the fine tuning of the R-ICP relationship may also include a calibration of the device and the relationship to an individual patient. For an example, if a patient has been admitted to a medical institution (e.g., emergency room, ICU) with suspected stroke or traumatic brain injury, and has already been implanted with an intracranial catheter for direct monitoring of ICP but the catheter later needs to be removed while the monitoring of ICP is still indicated, then initially while the catheter is still in, ICP may be simultaneously monitored both invasively and with non-invasive method 500, and these data used to additionally finely 'tune' the R-ICP curve to that particular patient. Subsequently, the catheter may be removed as indicated, and the monitoring of ICP will proceed with the non-invasive method 500 only.

The fine tuning of the R-ICP relationship may also include occasional calibrations of the device and the relationship on animal models or human subjects with increased ICP, as optical sensors are subject to drift over time.

Any combination of the acquired row signals and features derived as described above, including the numerical values of the estimated cerebral blood flow (CBF) and intracranial pressure (ICP) may be presented on a display. The exact choice of signals and/or features to be displayed, and of the ways they are displayed, are subject to considerations including their importance in a given clinical situation, the preference of a physician, ease of use and the like.

It should be appreciated that a device in accordance with embodiments of the present invention may be realized as either room-based or field-portable, depending on how the power supply is provided (wall power vs. batteries). Those skilled in the art will recognize that the optical measurements do not consume excessive power and can therefore be realized as a fully portable battery powered platform/device. The portability and ease of the device enables more frequent ICP assessment in the areas identified previously, as well as expansion of ICP assessment into areas heretofore considered economically or technically unfeasible. These new areas include first responders such as EMTs, medics, ambulances, and law enforcement officers; long term care situations such as nursing homes, assisted living, and home care; athletic trainers (during, for example, concussion assessment), and military battlefield applications.

Those of skill in the art will appreciate that the various illustrative functions, modules and method steps described in connection with the above described figures and the embodiments disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for ease of description. Specific functions can be moved from one module or step to another without departing from the invention.

Moreover, the various illustrative modules and method steps described in connection with the embodiments disclosed herein can be implemented or performed with a general purpose processor, a digital signal processor ("DSP"), an application specific integrated circuit ("ASIC"), field programmable gate array ("FPGA") or other programmable logic device, discrete gate or transistor logic, discrete hardware components, or any combination thereof designed to perform the functions described herein. A general-purpose processor can be a microprocessor, but in the alternative, the processor can be any processor, controller, or microcontroller, similar hardware. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer readable storage media including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. For example, while the change in volume of blood in the intracranial veins and jugular veins have specifically been discussed, any first and second source (e.g., veins) of blood in the brain may be used in accordance with some embodiments.

Thus, it is to be understood that the description and drawings presented herein represent exemplary embodiments of the invention and are therefore representative of the subject matter which is broadly contemplated by the present invention. It is further understood that the scope of the present invention fully encompasses other embodiments.

The invention claimed is:

1. A method of determining a change in intracranial pressure in a subject, the method comprising:
   measuring a change in volume of blood in the jugular veins of the subject;
   measuring a change in volume of blood in one or more intracranial veins of the subject;
   determining, by a processor, a ratio of the change in volume of the one or more intracranial veins to the change in volume of the one or more jugular veins;
   wherein changes in said ratio inversely corresponds to changes in the intracranial pressure of the subject.

2. The method of claim 1, further comprising:
   determining the absolute value of the intracranial pressure of the subject based on the ratio.

3. The method of claim 1, further comprising measuring the electrical activity of the brain of the subject and using the measured electrical activity to detect a silent seizure.

4. The method of claim 1, further comprising using rheoencephalography to detect a silent seizure.

5. The method of claim 1, wherein the measuring the changes in volume of blood is performed using one or more optical sensors.

6. An apparatus for determining a change in intracranial pressure in a subject, the apparatus comprising:
   an optical module configured to receive a first signal from a sensor indicative of a change in volume of blood in the jugular vein of the subject and a second signal indicative of a change in volume of blood in an intracranial vein of the subject; and
   a processor in communication with said optical module, the processor configured to receive the first and second signals, synchronize said signals, and determine an intracranial pressure measurement based on said signals.

7. The apparatus of claim 6, further comprising
   an electroencephalographic (EEG) module configured to receive an EEG signal; and
   wherein the processor is further configured to extract features from the EEG signal that are indicative of seizures.

8. The apparatus of claim 6 further comprising a rheoencephalography (REG) module configured to receive an REG signal and wherein the processor is further configured to determine cerebral blood flow based on the REG signal.

9. The apparatus of claim 7, wherein the processor is further configured to determine the ratio between the first signal and second signal.

10. The apparatus of claim 6, wherein the processor is further configured to determine cerebral blood flow based on the REG signal or the first signal.

11. The apparatus of claim 6, wherein the optical module comprises:
    a first light source; and
    a first light detector,
    wherein the first light detector is configured to detect light emitted from the first light source.

12. The apparatus of claim 6, wherein the apparatus is configured to be at or near the neck of the subject.

13. The apparatus of claim 11, wherein the further optical module comprises:
    a second light source; and
    a second light detector,
    wherein the second light detector is configured to detect light emitted from the second light source.

14. The apparatus of claim 6, wherein the optical module is configured to perform near-infrared spectroscopy (NIRS).

15. A method of determining a change in intracranial pressure in a subject, the method comprising:
    measuring a change in volume of blood in a first source in the brain of the subject;
    measuring a change in volume &blood in a second source in the brain of the subject; and
    determining, by a processor, a change in intracranial pressure based upon a ratio of the change in volume of the second source to the change in volume of the first source.

16. The method of claim 15, wherein the first and second sources are veins.

17. The method of claim 16, wherein the veins include the intracranial veins and jugular veins.

18. A method for detecting a change in transmission of pressure of a vein, comprising:

determining a change in pressure in a first vein which carries blood from the brain of a subject;
measuring a change in pressure in second vein which carries blood from the brain of the subject;
determining, by a processor, a ratio of the change in pressure of the first vein and the second vein; and
wherein changes in said ratio inversely corresponds to changes in the intracranial pressure of the subject.

19. The method of claim 18 further comprising measuring the electrical activity of the brain of the subject.

20. The method of claim 18, further comprising:
presenting the comparison to the pressure patterns to a user on a display.

* * * * *